(12) United States Patent
Okamoto et al.

(10) Patent No.: US 7,754,901 B2
(45) Date of Patent: Jul. 13, 2010

(54) METHOD FOR PRODUCING FLUORINATED COMPOUNDS AND POLYMERS

(75) Inventors: Yoshiyuki Okamoto, Fort Lee, NJ (US); Yasuhiro Koike, Yokohama (JP); Wei-Hong Liu, Dobbs Ferry, NY (US); Yinzhong Guo, Brooklyn, NY (US)

(73) Assignee: Japan Science and Technology Agency, Kawaguchi-shi (JP)

( * ) Notice: Subject to any disclaimer, the term of this patent is extended or adjusted under 35 U.S.C. 154(b) by 0 days.

(21) Appl. No.: 12/510,003

(22) Filed: Jul. 27, 2009

(65) Prior Publication Data

US 2009/0326178 A1    Dec. 31, 2009

Related U.S. Application Data

(62) Division of application No. 10/580,977, filed as application No. PCT/JP2004/017905 on Nov. 25, 2004, now Pat. No. 7,582,714.

(60) Provisional application No. 60/525,865, filed on Dec. 1, 2003.

(30) Foreign Application Priority Data

Jun. 16, 2004    (JP)    ................ 2004-178766

(51) Int. Cl.
C08F 116/16    (2006.01)
C07D 317/00    (2006.01)

(52) U.S. Cl. .................... 549/455; 526/247
(58) Field of Classification Search ............ 549/455
See application file for complete search history.

(56) References Cited

U.S. PATENT DOCUMENTS

| | | | |
|---|---|---|---|
| 3,308,107 A | 3/1967 | Selman et al. | |
| 3,356,677 A * | 12/1967 | Cross et al. | 540/15 |
| 3,749,794 A * | 7/1973 | Terrell et al. | 514/467 |
| 4,429,143 A * | 1/1984 | Anderson et al. | 549/450 |
| 4,496,750 A * | 1/1985 | Anderson et al. | 549/455 |
| 4,558,141 A * | 12/1985 | Squire | 549/455 |
| 4,594,399 A | 6/1986 | Anderson et al. | |
| 5,057,586 A | 10/1991 | Krespan | |
| 5,080,508 A | 1/1992 | Onishi et al. | |
| 5,233,058 A * | 8/1993 | Anton et al. | 549/450 |
| 5,235,074 A | 8/1993 | Navarrini et al. | |
| 5,276,121 A | 1/1994 | Resnick | |
| 5,336,741 A | 8/1994 | Yang | |
| 5,408,020 A | 4/1995 | Hung et al. | |
| 5,750,730 A * | 5/1998 | Nakano et al. | 549/229 |
| 6,066,707 A | 5/2000 | Colaianna et al. | |
| 6,627,382 B2 | 9/2003 | Kim | |
| 6,750,294 B2 | 6/2004 | Sugiyama et al. | |
| 7,271,229 B2 | 9/2007 | Okazoe et al. | |
| 2005/0037265 A1 * | 2/2005 | Watakabe | 429/309 |
| 2006/0194936 A1 | 8/2006 | Eriguchi et al. | |

OTHER PUBLICATIONS

He, et al., "A remarkable [2.2.2]propellane," *J Am Chem Soc.*, vol. 125, 5590-5591, Apr. 18, 2003.
Liu, et al., "A Novel Thermally and Chemically Stable Polymer: Poly(2-difluoromethylene-1,3-dioxolane)," *Macromolecules*, vol. 37, 254-255, 2004.
Liu, et al., "Free-Radical Polymerization of Dioxolane and Dioxane Derivatives: Effect of Fluorine Substituents on the Ring Opening Polymerization," *J Polym Sci A*, vol. 42, 5180-5188, 2004.
International Search Report and Written Opinion for PCT/JP2004/017905 dated Feb. 7, 2005.

* cited by examiner

*Primary Examiner*—Bernard Lipman
(74) *Attorney, Agent, or Firm*—Marshall, Gerstein & Borun LLP

(57) ABSTRACT

A fluorinated polymer comprising a unit represented by the following formula (1), a method for producing fluorinated compounds and the fluorinated polymers, and an optical/electrical material or coating material comprising the fluorinated polymer.

3 Claims, 4 Drawing Sheets

METHOD FOR PRODUCING FLUORINATED COMPOUNDS AND POLYMERS

CROSS-REFERENCE TO RELATED APPLICATIONS

This is a division of U.S. application Ser. No. 10/580,977 filed May 31, 2006, now U.S. Pat. No. 7,582,714, which is the U.S. National Phase of PCT/JP2004/017905 filed Nov. 25, 2004, based on U.S. Provisional application Ser. No. 60/525,865 filed Dec. 1, 2003, and JP 2004-178766 filed Jun. 16, 2004, the entire respective disclosures of which are incorporated herein by reference.

BACKGROUND OF THE INVENTION

1. Field of the Invention

The present invention relates to novel fluorinated polymers and method for producing fluorinated compounds and fluorinated polymers.

2. Description of the Related Art

Fluorinated polymers are useful materials that are used in various applications, for example, optical members such as plastic optical fibers and photoresist materials, or surface modifiers. However, the synthetic processes of fluorinated polymers are complicated and costly.

A fluorinated polymer is obtained by polymerization of a fluorinated compound having a polymerizable unsaturated group. As an example of fluorinated polymers, 1,3-dioxolane derivatives and the like are disclosed in U.S. Pat. No. 3,308,107, U.S. Pat. No. 3,450,716; Izvestiya A Kademii Nank SSSR, Seriya Khimicheskaya. pp. 392-395, February 1988 by V. S. Yuminov et al. and pp/938-, April 1989 by V. S. Yuminov et al; and the like.

SUMMARY OF THE INVENTION

The present inventors have developed the following useful and novel fluorinated polymers and synthetic methods. The present invention will be described below.

A first aspect of the present invention is a fluorinated polymer comprising an unit represented by the following formula (1):

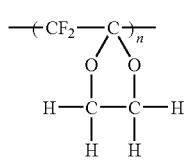

Formula (1)

A second aspect of the present invention is the fluorinated polymer according the first aspect, wherein the fluorinated polymer is a homopolymer.

A third aspect of the present invention is the fluorinated polymer according the first aspect, wherein the fluorinated polymer is represented by the following formula (2),

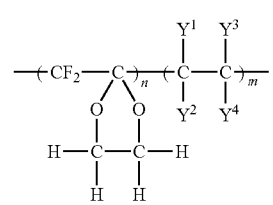

Formula (2)

wherein: in Formula (2), $Y^1$ to $Y^4$ each independently represent a hydrogen atom, fluorine atom, or chlorine atom.

A fourth aspect of the present invention is a method for producing fluorinated compounds, in which a compound represented by the following formula (4) is produced by reaction of 2-chloro-2,2-difluoroethane-1,1-diol and at least one compound represented by the following formula (3):

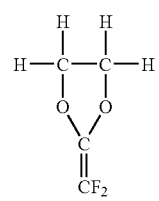

Formula (4)

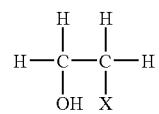

Formula (3)

wherein: in Formula (3), X represents a hydroxy group, a chlorine atom, or bromine atom.

A fifth aspect of the present invention is a method for producing fluorinated compounds, in which a compound represented by the following formula (4) is produced by reaction of 2-chloro-2,2-difluoroacetaldhyde and ethyleneoxide.

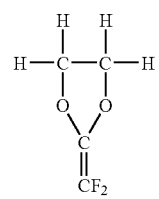

Formula (4)

A sixth aspect of the present invention is a method for producing fluorinated polymers, in which a polymer comprising an unit represented by the following formula (1) is produced by polymerization the fluorinated compound represented by the following formula (4) obtained by the method according to the fourth aspect.

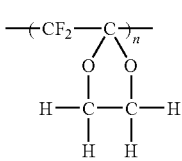

Formula (1)

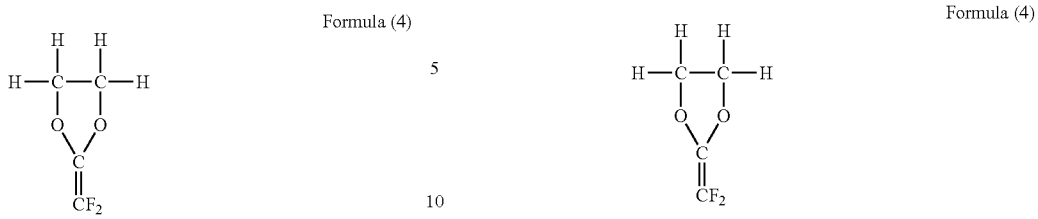

Formula (4)

A seventh aspect of the present invention is a method for producing fluorinated polymers, in which a polymer comprising an unit represented by the following formula (1) is produced by polymerization the fluorinated compound represented by the following formula (4) obtained by the method according to the fifth aspect.

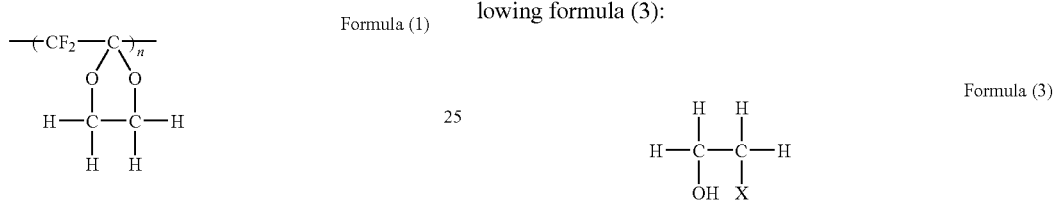

Formula (1)

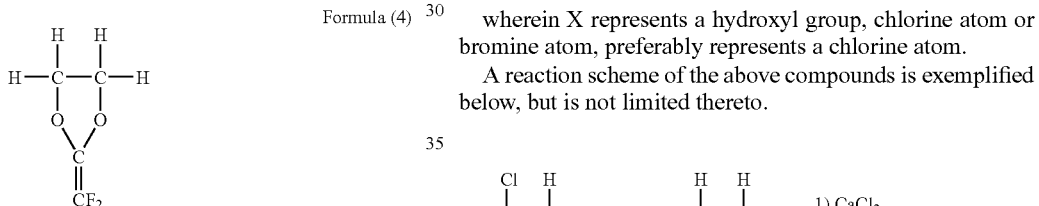

Formula (4)

A eighth aspect of the present invention is an optical/electrical material or coating material comprising the fluorinated polymer according to the first aspect.

DETAILED DESCRIPTION OF THE INVENTION

1. Method for Producing Fluorinated Compounds

Figure 1:
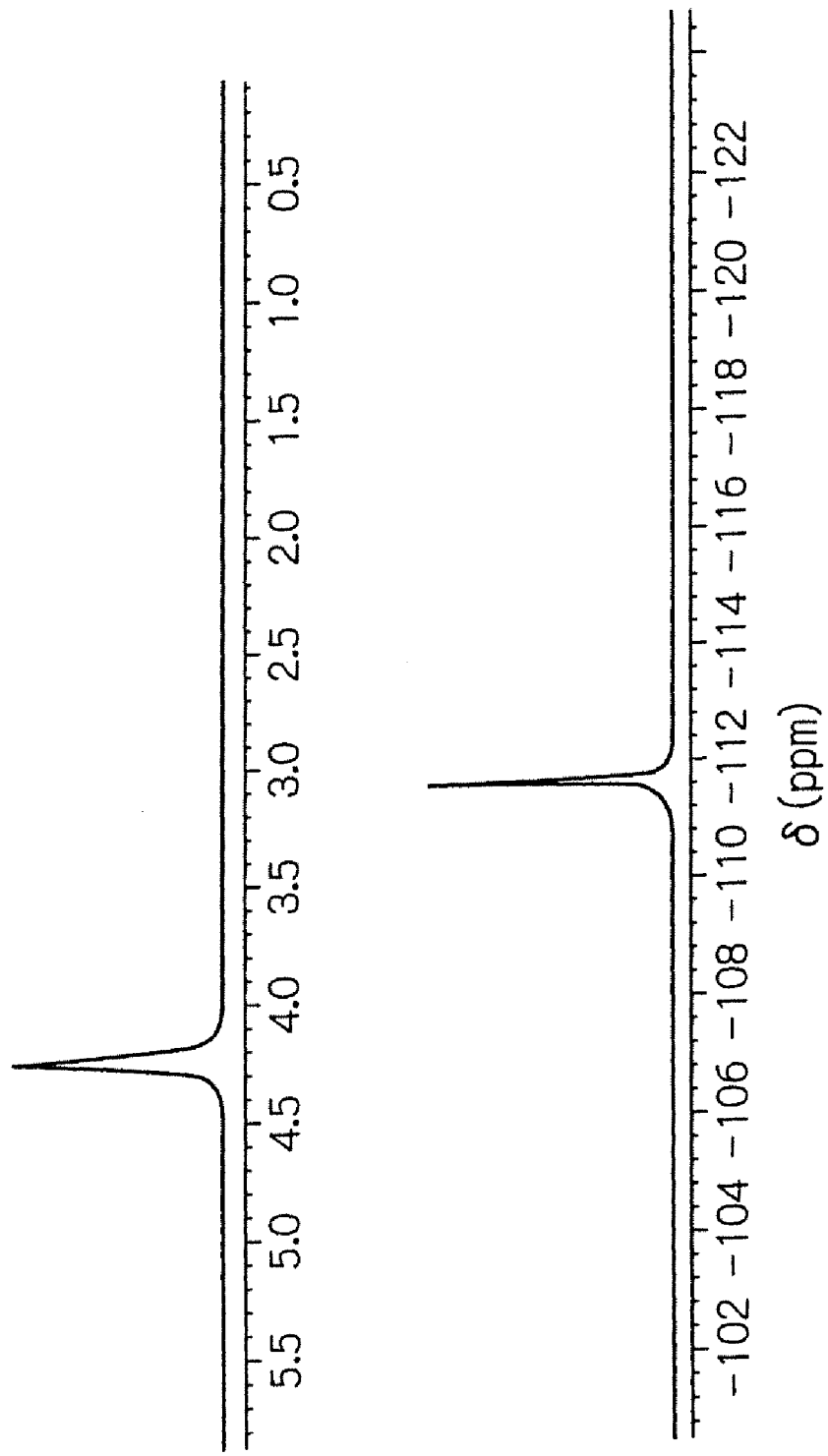
FIG. 1 is a graph illustrating a $^1$HNMR spectrum and a $^{19}$FNMR spectrum of a polymer synthesized in Example 2.

The polymer of the present invention is obtained by polymerizing a 1,3-dioxolane derivative represented by the following formula (4):

Formula (4)

First, the producing process of the fluorine-containing compound represented by the above formula (4) will be described. Here, two producing processes according to the present invention will be described.

1-1 First Producing Method

The above fluorine-containing compound which is a 1,3-dioxolane derivative is produced by using 2-chloro-2,2-difluoroethane-1,1-diol and a compound represented by the following formula (3):

Formula (3)

wherein X represents a hydroxyl group, chlorine atom or bromine atom, preferably represents a chlorine atom.

A reaction scheme of the above compounds is exemplified below, but is not limited thereto.

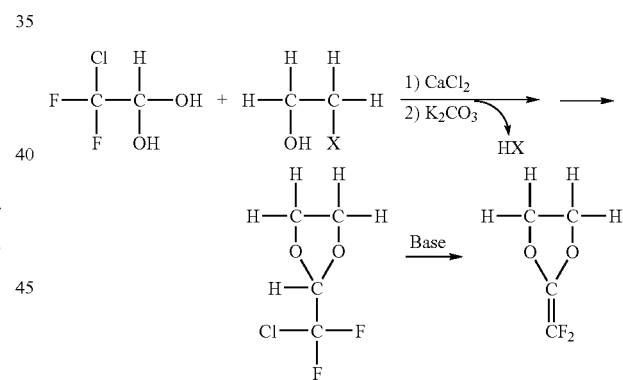

The first producing method of the present invention includes the following two steps, and is a simple and inexpensive method:

(1) the step of conducting de-hydrogen halide while performing dehydration from 2-chloro-2,2-difluoroethane-1,1-diol and at least one compound represented by the formula (3) by the use of calcium chloride and potassium carbonate, and (2) the step of conducting de-hydrogen halide, with a base.

The steps of (1) and (2) will be described hereinafter.

Step (1)

2-Chloro-2,2-difluoroethane-1,1-diol and the compound represented by the formula (3) are preferably allowed to react with each other in equimolecular amounts. The compounds represented by the formula (3) may be used singly or in combination of two or more kinds of the compounds. However, a single kind of the compound is preferably used.

Sodium carbonate or the like may be used in place of calcium chloride and potassium carbonate.

As the reaction is an exothermic reaction, the reaction is preferably carried out while cooling. Other reaction conditions are not specifically limited, and a purifying process such as distillation may be preferably performed prior to the step (2)

Step (2)

The compound obtained by Step (1) is subjected to a de-hydrogen halide process. The elimination process of the hydrogen halide is carried out by using a strong base such as potassium hydroxide in an alcohol such as ethanol. As the base, potassium t-butoxide or the like may be used.

In the producing process of the present invention, steps other than steps (1) and (2) may be performed.

1-2 Second Producing Method

2-Chloro-2,2-difluoroacetaldehyde is allowed to react with ethylene oxide to form 1,3-dioxolane derivative-fluorine-containing compound represented by the above formula (4). The reaction scheme of these compounds is shown below, but is not restricted thereto.

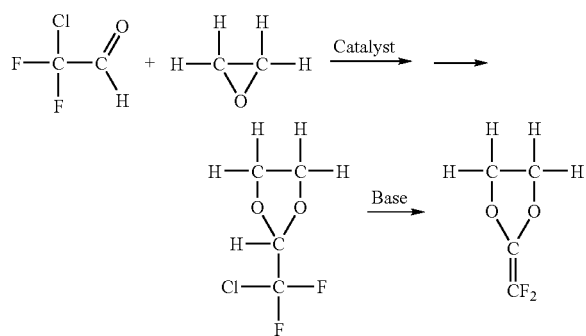

The second producing method of the present invention includes the following two steps, and is a simple and inexpensive method:

(1) the step of conducting a catalytic reaction of 2-chloro-2,2-difluoro-acetaldehyde and ethylene oxide, and the step of conducting de-hydrogen halide by use of a base.

The steps (1) and (2) will be described hereinafter.

Step (1)

2-Chloro-2,2-difluoroacetaldehyde and ethylene oxide are preferably allowed to react with each other in equimolecular amounts.

As a catalyst, $NiCl_2$, $CuCl_2$, $ZnCl_2$ and the like can be used. The amount of the catalyst is approximately in the range of 0.001 to 0.01 mole per mole of each compound.

As the reaction is an exothermic reaction, the reaction is preferably carried out while cooling. Other reaction conditions are not specifically limited, and a purifying process such as distillation may be preferably performed prior to the step (2)

Step (2)

The compound obtained by step (1) is subjected to a de-hydrogen halide process. The elimination process of the hydrogen halide is carried out by using a strong base such as potassium hydroxide in an alcohol such as ethanol. As the base, potassium t-butoxide or the like may be used.

In the producing process of the present invention, steps other than steps (1) and (2) may be performed.

2. Method of Producing Fluorine-Containing Polymer 1,3-Dioxolane derivative represented by the above formula (4) can be easily polymerized by using a radical polymerization initiator to form a polymer represented by the following formula (1):

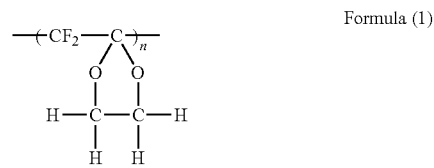

Formula (1)

The above 1,3-dioxolane derivative represented by the above formula (4) is a 5-membered cyclic compound and a stable substance. In case of 6-membered cyclic ring compound, the compound is apt to open the ring during polymerization process so that the resultant polymer becomes a mixture, resulting in decrease in physical properties such as heat resistance and hydrolysis.

The polymer having the following structure (1) can be produced by a conventional radical polymerization process. As radical polymerization catalysts, conventional substances can be used. For example, peroxides, and azo type polymerization initiators such as AIBN (2,2-azobisisobutyronitril) can be used.

When only 1,3-dioxolane derivative represented by the above formula (4) is used as a monomer starting material, a homopolymer is obtained. When 1,3-dioxolane derivative represented by the above formula (4) and another monomer are used in combination, a copolymer of the compound represented by the formula (4) and the other monomer is obtained. Another monomer is not specifically limited, as long as the monomer is a compound having a carbon double bond. Such copolymer includes the polymer represented by the following formula (2):

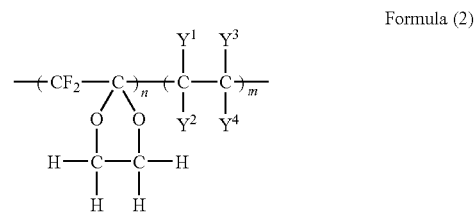

Formula (2)

wherein $Y^1$ to $Y^4$ each independently represent a hydrogen atom, a fluorine atom or a chlorine atom. Preferably, $Y^1$ to $Y^4$ each independently represent a fluorine atom or a chlorine atom.

The ratio of n to m is preferably 1:9 to 5:5, and more preferably 2:8 to 3:7.

3. Fluorine-Containing Polymer

The polymer having structure of formula (1) is insoluble in a solvent such as acetone, DMSO, toluene THF, chloroform and methanol, but soluble in fluorination solvent such as hexafluoroisopropanol (HFIP) and chloroform containing a small amount of trifluoroacetic acid.

The polymer having structure of formula (1) has a high melting point, and a high glass transition temperature, and is an extremely thermally stable substance. In particular, a homopolymer having structure of formula (1) is a paracrystal body and has a high melting point, and is an extremely thermally stable substance. Further, the polymer having structure of formula (1) is still stable in sulfuric acid and a heated concentrated aqueous solution of potassium hydroxide.

It is reported that when 2-methylene-1,3-dioxolane in which all fluorine atoms of the compound represented by the above formula (4) are substituted with hydrogen atoms is radical-polymerized, the resultant polymer is partially ring-opened (W. J. Bailey, Z. Ni. and S. Wu; J. Poly. Sci. Polymer Chem. Ed. 20, 3021 (1982)).

When 2-difluoromethylene-1,3-dioxane which has 6-membered ring is radical-polymerized, the compound is apt to open the ring, and therefore, the resultant polymer is a copolymer and/or a mixture of a vinyl addition polymerized polymer and a ring-opened polymer, so that the polymer tends to cause deterioration of physical properties such as acid-resistant, alkali-resistant and heat resistant properties. On the other hand, when the compound represented by the above formula (4) is subjected to a radical polymerization reaction by use of a radical initiator, the resultant polymer is only a vinyl addition polymer and ring-opened polymer is hardly obtained. If resultant polymer is not a mixture, the polymer has a higher melting point and a higher glass transition temperature. Accordingly, the polymer having the structure of the formula (1) is chemically and thermally stable. That is, the polymer having the structure of the formula (1) has a high crystallinity, and excellent heat and photo resistance, and therefore, can be used for a special paint and the like.

The copolymer represented by the above formula (2) is soluble in fluorination solvent such as hexafluoroisopropanol (HFIP) and chloroform containing a small amount of trifluoroacetic acid.

In comparison with the homopolymer and the copolymer, tetrafluoroethylene polymer which is a fluorine-containing polymer is slightly soluble in solvent. That is, the homopolymer and the copolymer represented by the formula (2) of the present invention has a high adhesiveness with the surface of metal or glass due to its solubility, and is applicable to a new thin layer coating material and insulating material.

Further, when the surface of the film of the homopolymer and the copolymer is oxidized with dilute nitric acid or potassium permanganate, the surface can have the following functional groups:

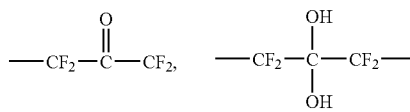

The adhesiveness of the surface can greatly be improved by providing with such functional groups on the surface.

The homopolymer and the copolymer of the invention can be utilized for being cast into films, i.e. to prepare solutions for coating on metal, glass and other subjects. The thin film formed is very stable with respect to chemicals and heat as well as with respect to light. Thus, it is especially useful as a protective coating material.

Next, the present invention will be explained with reference to Examples, but is not limited thereto.

Example 1

Synthesis of Chlorodifluoroacetaldehyde

Chlorodifluoroacetaldehyde was obtained by reducing methylchlorodifluoro acetate with lithium aluminum hydride.

100 g (0.69 mole) of methylchlorodifluoro acetate was added to 100 ml of anhydrous ether, and placed in a 1 liter-sized three-neck flask having a stirrer, funnel and reflux condenser. The flask was cooled in a dry ice/acetone bath. In a separate operation, 7 g (0.18 mole) of lithium aluminum hydride was added to 150 ml of ether solution, and thus obtained slurry was stirred for 2 hours. After stirring, the ether solution of lithium aluminum hydride was added dropwise to methylchlorodifluoro acetate separately prepared over three hours. After adding lithium aluminum hydride, 20 ml of 95% by mass of ethanol was added to the reaction mixture maintained at −78° C. Thereafter, the mixture was brought to room temperature. In order to dissolve the aluminum compound, the resultant reaction mixture was poured into a 2-liter-sized beaker accommodated with crashed ice and concentrated hydrochloric acid. The mixture was separated into two phases, and the aqueous phase was extracted with ether. The ether portion was distilled at 95° C. to 100° C. without drying. The obtained distillate was almost chlorodifluoroacetaldehyde hydrate ($CClF_2CH(OH)_2$). The yield was 75%.

Synthesis of 2-Chlorodifluoromethyl-1,3-Dioxolane 157 g (1.4 mole or less) of $CClF_2CH(OH)_2$, 197 g (1.5 mole) of 2-bromoethanol and 20 g of calcium chloride were placed in a 1 liter-sized flask with a condenser. The flask was heated at 90° C. for 7 hours and cooled to room temperature. The upper phase was transferred to a 5 liter-sized flask, and 2 liters of acetone and 386 g (2.8 moles) of potassium carbonate were added to the flask. The mixture was reacted at 50° C. for three days, and a solid was precipitated. The solvent was removed by distillation. The product was purified by distillation. The yield of the product was 88% (195 g) and has a boiling point of 62° C./30 mmHg.

$^1$HNMR was 5.24 ppm (t, 1H, —CH—), 3.94-4.3 ppm (m, 4H, —$OCH_2$—). $^{19}$FNMR (ppm) was −70.56 ppm (2F, —$CF_2$—).

Synthesis of 2-Difluoromethylene-1,3-Dioxolane 50 g (0.31 mole) of 2-chlorodifluoromethyl-1,3-dioxolane and 800 ml of THF were placed in a flask placed in an ice bath. 37 g (0.33 mole) of potassium t-butoxide was added dropwise to the flask. The reaction was monitored by $^{19}$FNMR measurement. The signal at 70.56 ppm attributed to 2-chlorodifluoromethyl-1,3-dioxolane decreased, and the signal at −136.75 ppm attributed to >C═$CF_2$ increased with the passage of time. After 85% or more of hydrogenchloride was removed, the monomer was collected in a cold trap (−78° C.) by use of THF under reduced pressure.

Since 2-difluoromethylene-1,3-dioxolane, which is a reaction product, is apt to be polymerized by heating, the solution was concentrated by removing THF under vacuum at 0° C. 22.7 g of the monomer at a concentration of 0.4M was contained in the THF solution. The yield was 60%. The THF solution was used for radical polymerization.

$^1$HNMR $CDCl_3$) δ (ppm): 4.36 (s, 4H)
$^{19}$FNMR ($CDCl_3$) δ(ppm): −136.04 (s, —$CF_2$—)

Polymerization of 2-chlorodifluoromethylene-1,3-dioxolane

A solution containing 40 mmol of the monomer obtained in Example 1(2-chlorodifluoromethylene-1,3-dioxolane) and 100 ml of THF, and 65 mg of AIBN (0.4 mmol) were placed in a glass tube, and degassed thereof. Thereafter, argon was charged into the glass tube by a 3-cycle vacuum cooler, and the glass tube was sealed, and heated at 60° C. for one day. The polymer was condensed during polymerization. The condensed product was added to methanol, and precipitated from hexafluoroisopropanol solution for purification. The yield of 2-chlorodifluoromethyl-1,3-dioxolane polymer was 80% and obtained in an amount of 3.9 g.

Example 2

Synthesis of 2-Chlorodifluoromethyl-1,3-Dioxolane 114.5 g (1.11 mole) of 2-chloro-2,2-difluoroacetaldehyde, 44 g (1 mole) of ethylene oxide and 1.3 g (0.01 mole) of $NiCl_2$ were placed in a 1 liter-sized flask with a condenser. The flask was heated at 90° C. for 7 hours and cooled to room temperature. The upper phase was transferred to a 5 liter-sized flask, to which 2 liters of acetone and 386 g (2.8 moles) of potassium carbonate were added. The mixture was maintained at 50° C. for 3 days, resulting in precipitating a solid. The solvent was removed by distillation. The reaction product was purified by distillation. The yield was 88% (129.4 g), and the boiling point of the product was 62° C./30 mm Hg.

$^1$HNMR was 5.24 ppm (t, 1H, —CH—), 3.94-4.3 ppm (m, 4H, —OCH$_2$—). $^{19}$FNMR (ppm) was −70.56 ppm (2F, —CF$_2$—).

Synthesis of 2-Difluoromethylene-1,3-Dioxolane 2-difluoromethylene-1,3-dioxolane was obtained in a similar manner as Example 1 by the use of 2-chlorodifluoromethyl-1,3-dioxolane obtained in the above.

Polymerization of 2-Difluoromethylene-1,3-Dioxolane 2-difluoromethylene-1,3-dioxolane could be polymerized in a similar manner as Example 1.

Example 3

Copolymer of 2-difluoromethylene-1,3-dioxolane with tetrafluoroethylene

A 200 ml solution of 1,1,2-trichlorotrifluoroethane containing 6 g of 2-difluoromethylene-1,3-dioxolane and 0.02 g of perfluoropropionyl peroxide were loaded into 1 L autoclave at liquid nitrogen temperature for polymerization, equipped for stirring and opening for the loading and unloading of the reactants. After the solution was degassed under reduced pressure and the autoclave was refilled with argon, 16 g of tetrafluoroethylene was introduced at liquid nitrogen temperature. The reactor was gradually brought to room temperature and then heated at 40-45° C. for 10 hrs. The unreacted monomer and solvent were removed to traps at −78° C. under reduced pressure. After distillation of the solvent and the unreacted monomer, the solid product was further heated under a vacuum at a temperature of 100° C. for 5 hrs. 22 g of the solid product was isolated. TGA showed a weight loss of 2% at 450° C. $^{19}$FNMR analysis indicated that the composition ratio of the dioxolane and tetrafluoroethylene was 0.5 to 2.0, and the product was dissolved in fluorinated solvent such as hexafluorobenzene.

Example 4

Copolymer of 2-Difluoromethylene-1,3-Dioxolane with Tetrafluoroethylene

A 150 ml solution of 1,1,2-trichlorotrifluoroethane containing 3 g of 2-difluoromethylene-1,3-dioxolane and 0.02 g of perfluoro-t-butyl peroxide were loaded into a 1 L autoclave at liquid nitrogen temperature for polymerization. After the solution was degassed under reduced pressure and the autoclave was refilled with argon, 32 g of tetrafluoroethylene was introduced at liquid nitrogen temperature. The reaction was carried out as described in Example 3. 29 g of the solid product was obtained, and the ratio of the dioxolane and tetrafluoroethylene in the copolymer obtained was found to be 0.5 to 10.

Example 5

Characteristics of 2-Chlorodifluoromethyl-1,3-Dioxolane Polymer

The resultant polymer was not dissolved in solvents such as acetone, DMSO, toluene, THF, chloroform and methanol, but was dissolved in a fluorination solvent such as hexafluoroisopropanol (HFIP) and trifluoroacetic acid (TFA).

The intrinsic viscosity (η) of the polymer was 0.38 dL/g in a mixed solvent of chloroform and trifluoroacetic acid (volume ratio: 9/1) at 25° C. $^1$HNMR and $^{19}$FNMR spectra of the obtained polymer were measured by Bruker AC 300 spectrophotometer. Mixed solvent of chloroform and trifluoroacetic acid (volume ratio: 9/1) was used as solvent. As an internal standard, TMS for $^1$HNMR measurement, and trichlorofluoromethane for $^{19}$FNMR measurement were used, respectively. The results of the measurements are shown in FIG. 1.

The peak attributed to fluorinated vinyl group is not shown in $^1$HNMR. The peak at 112.00 ppm is characteristic of a saturated fluorine compound (—CF$_2$—) in the main chain. Only one peak in $^1$HNMR appeared at 4.26 ppm, which was identified as a proton on a dioxolane ring. The existence of opened ring products was not confirmed by the IR and NMR measurements, and it was found that only vinyl addition reaction occurred.

Figure 2:
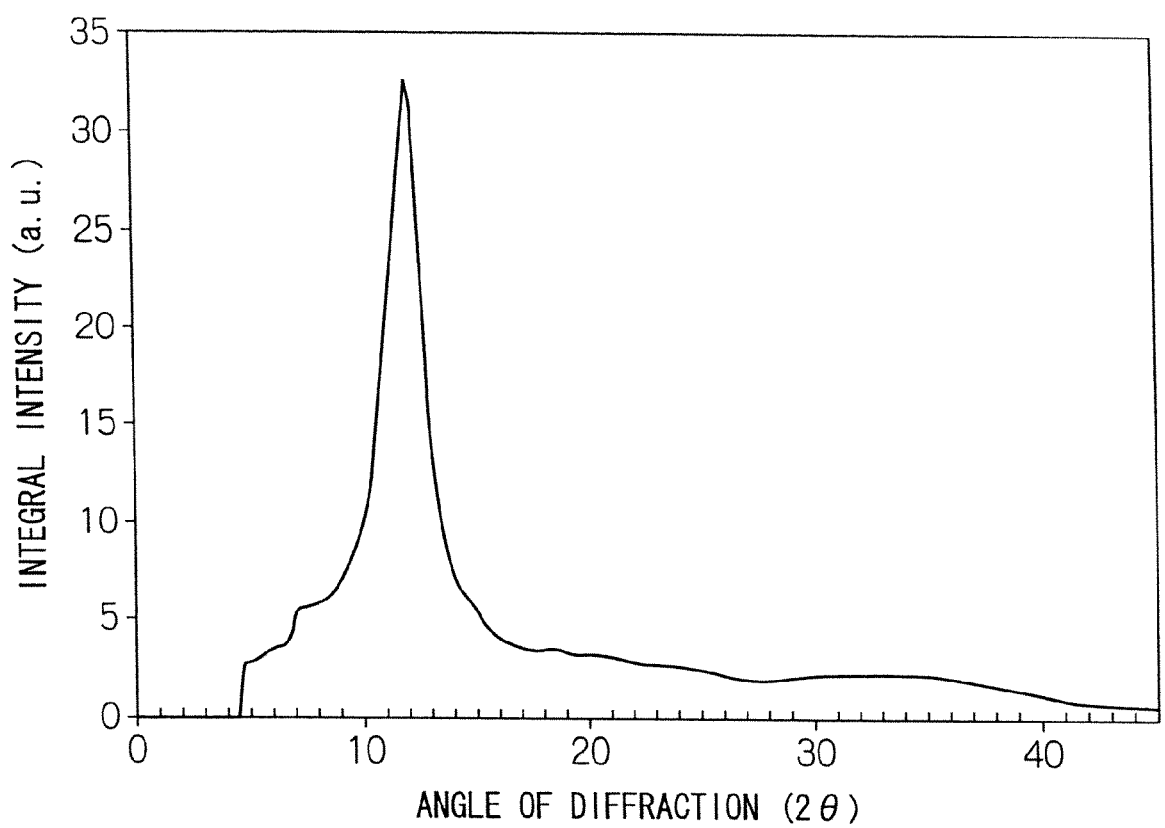
FIG. 2 is a graph illustrating an X-ray diffraction pattern of a polymer synthesized in Example 2.

As shown in FIG. 2, the X-ray diffraction pattern of the polymer powder showed that the polymer was a paracrystal body, and the crystallinity thereof was approximately 44%. The melting point of the polymer was 356° C. which was higher than that of polyfluonated ethylene, 327° C.

Figure 3:
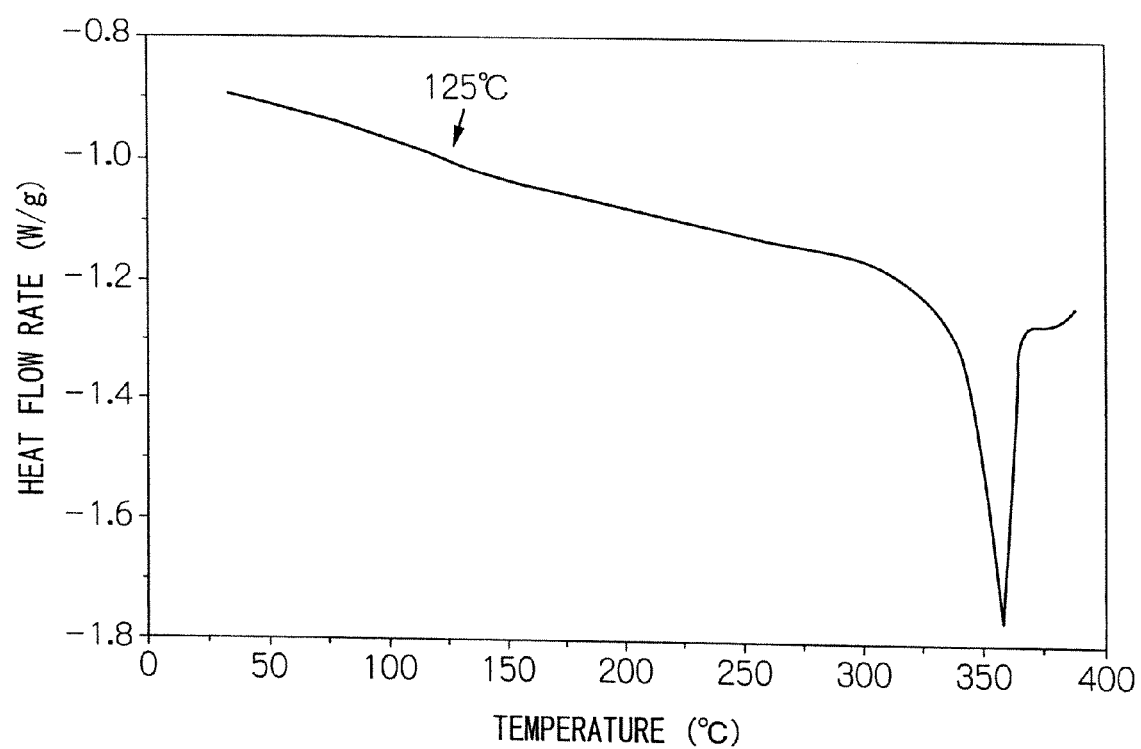
FIG. 3 is a graph illustrating a glass transition temperature of a polymer synthesized in Example 2.
Figure 4:
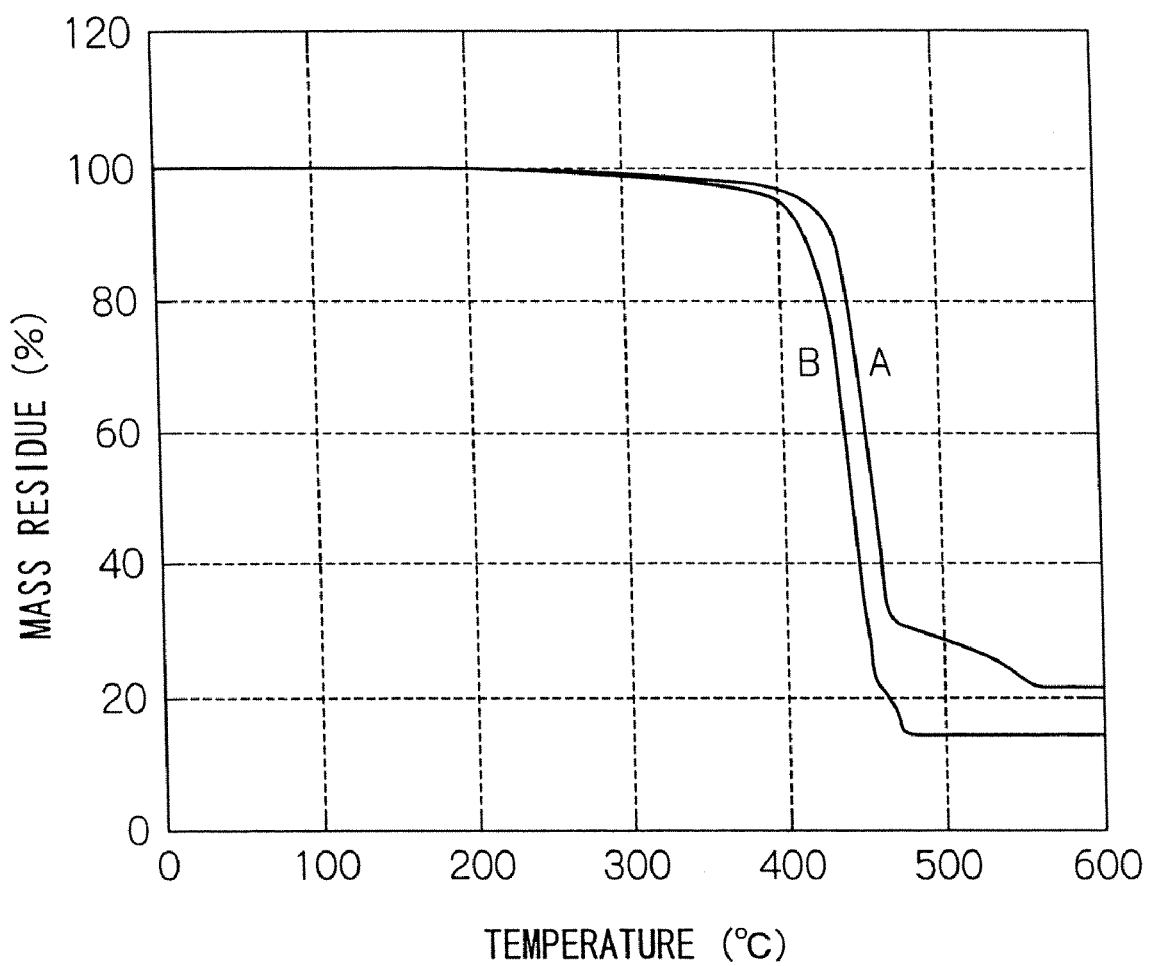
FIG. 4. is a graph illustrating a thermal decomposition of a polymer synthesized in Example 2. A; in nitrogen gas atmosphere, B; in air atmosphere.

As shown in FIG. 3, the glass transition temperature of the polymer of the present invention was 125° C. The polymer showed a high thermal stability under a nitrogen gas atmosphere as a result of a thermogravimetric analysis. As shown in FIG. 4, a thermal decomposition of the polymer was started at 427° C. under a nitrogen gas atmosphere (A) and started at 414° C. under an air atmosphere (B).

A transparent thin polymer film (0.1 mm or less in thickness) was obtained by casting an HFIP solution containing the polymer on a glass substrate or a silicon substrate. The thin film thus prepared was placed on a Metricon model 2010 prism coupler, and the refractive index thereof was measured. The refractive index of the film was 1.4396 at the wavelength of 632.8 nm, and 1.4372 at the wavelength of 1544 nm, respectively.

The thin film having a thickness of 0.5 mm or less was immersed in each of 20% by mass of an aqueous sulfuric acid solution, and 30% by mass of an aqueous sodium hydroxide solution at 60° C. for two days. Thereafter, the films were washed with water and dried. An IR spectrum and mass measurements were carried out for the dried films, and deterioration of the performance of the films was not found.

As described above, the resultant polymer was extremely thermally and chemically stable, and suitable for materials for electrical components and optical elements, in particular, most suitable for application for special paint use.

Example 6

The copolymer obtained in example 1 was casted on glass plate. The polymer coated plate (polymer thickness=0.1-0.3 mm) was treated with HNO3/H2SO4 at 50-60° C. for 5 hrs. After the film was washed thoroughly with water and dried at 100° C. under vacuum, the surface was examined by IR measurements. The spectra indicated that —OH and —C=O— groups were produced on the surface. The adhesivity of the film toward aluminum and glass was greatly increased.

The invention claimed is:

1. A method for producing fluorinated compounds, comprising producing a compound represented by formula (4) by reacting
2-chloro-2,2-difluoroethane-1,1-diol and at least one compound represented by formula (3)

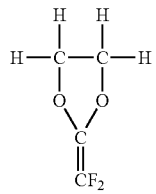

Formula (4)

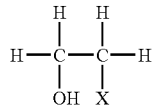

Formula (3)

wherein in Formula (3), X represents a hydroxy group, a chlorine atom, or a bromine atom.

2. A method for producing fluorinated compounds, comprising producing a compound represented by formula (4), by reacting 2-chloro-2,2-difluoroacetaldhyde and ethylene oxide.

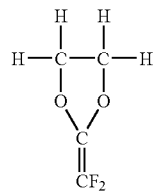

Formula (4)

3. A method for producing fluorinated polymers, comprising producing a polymer represented by formula (1) by polymerizing the fluorinated compound represented by formula (4) obtained by the method according to claim 2.

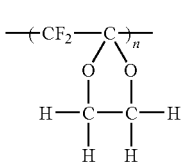

Formula (1)

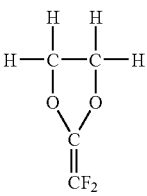

Formula (4)

* * * * *